(12) United States Patent
Barabás et al.

(10) Patent No.: US 12,279,826 B2
(45) Date of Patent: Apr. 22, 2025

(54) EXOSKELETON FOR ASSISTING SURGICAL POSITIONING, METHOD FOR PRODUCING THE EXOSKELETON

(71) Applicant: SEMMELWEIS EGYETEM, Budapest (HU)

(72) Inventors: János Imre Barabás, Érd (HU); István Hartyánszky, Budapest (HU); Béla Péter Merkely, Budapest (HU)

(73) Assignee: Semmelweis Egyetem, Budapest (HU)

( * ) Notice: Subject to any disclaimer, the term of this patent is extended or adjusted under 35 U.S.C. 154(b) by 879 days.

(21) Appl. No.: 17/292,103

(22) PCT Filed: Nov. 8, 2019

(86) PCT No.: PCT/HU2019/050049
§ 371 (c)(1),
(2) Date: May 7, 2021

(87) PCT Pub. No.: WO2020/095078
PCT Pub. Date: May 14, 2020

(65) Prior Publication Data
US 2021/0393329 A1 Dec. 23, 2021

(30) Foreign Application Priority Data

Nov. 9, 2018 (HU) ..................................... 1800379

(51) Int. Cl.
*A61B 34/10* (2016.01)
*A61B 17/00* (2006.01)
(Continued)

(52) U.S. Cl.
CPC ........ *A61B 34/10* (2016.02); *A61B 17/32053* (2013.01); *B33Y 10/00* (2014.12);
(Continued)

(58) Field of Classification Search
CPC .............. A61M 60/178; A61M 60/232; A61M 60/865; A61M 60/148; A61M 60/161;
(Continued)

(56) References Cited

U.S. PATENT DOCUMENTS

| 8,303,505 B2 | 11/2012 | Webler et al. |
| 2002/0168618 A1 | 11/2002 | Anderson et al. |

(Continued)

FOREIGN PATENT DOCUMENTS

| CN | 106361429 A | 2/2017 |
| GB | 1 447 394 | 8/1976 |

(Continued)

*Primary Examiner* — Kelly J Bekker
*Assistant Examiner* — Andrew P. Restaino
(74) *Attorney, Agent, or Firm* — Jason D. Voight (57) ABSTRACT

The exoskeleton (10) for assisting surgical positioning is made of biocompatible material and formed to be substantially form-preserving. The exoskeleton (10) comprises a shell (11) having a coupling surface (15*b*) fitting to at least a part of a surface of an organ to be operated, and a guiding channel (13) is formed in the shell (11) at a predetermined position, said guiding channel having a predetermined orientation with respect to said shell and a predetermined cross-sectional area for directing a surgical tool to the organ to be operated.

10 Claims, 4 Drawing Sheets

(51) Int. Cl.
  *A61B 17/32*    (2006.01)
  *A61B 17/3205*  (2006.01)
  *B33Y 10/00*    (2015.01)
  *B33Y 80/00*    (2015.01)

(52) U.S. Cl.
  CPC ..... *B33Y 80/00* (2014.12); *A61B 2017/00526* (2013.01); *A61B 2017/00871* (2013.01); *A61B 2017/320052* (2013.01); *A61B 2034/105* (2016.02); *A61B 2034/108* (2016.02)

(58) Field of Classification Search
  CPC ... A61M 60/165; A61M 60/191; B33Y 50/02; B33Y 10/00; B33Y 80/00; A61B 2017/3405; A61B 2017/3407; A61B 2017/3425; A61B 34/10; A61B 17/32053; A61B 2017/00526; A61B 2017/00871; A61B 2017/320052; A61B 2034/105; A61B 2034/108; A61B 2017/00238; A61B 2017/00243; A61B 2017/00247; A61B 90/10; A61B 90/11; A61B 90/17; A61B 17/34; A61B 17/3403; A61B 17/3462; A61B 2017/3411; A61B 2017/3482; A61B 2017/3484; A61B 2017/3488; A61B 2017/3492; A61B 17/32; A61B 17/320016; A61B 17/3209; A61F 2/2478; A61F 2/2481; A61F 2002/2484

See application file for complete search history.

(56) References Cited

U.S. PATENT DOCUMENTS

| | | |
|---|---|---|
| 2003/0078592 A1* | 4/2003 | Heilman ............ A61M 60/859 606/108 |
| 2006/0195004 A1 | 8/2006 | Jarvik |
| 2007/0015958 A1* | 1/2007 | Lau ................. A61B 17/00234 600/37 |
| 2008/0058603 A1* | 3/2008 | Edelstein .......... A61B 17/3403 600/201 |
| 2014/0073907 A1 | 3/2014 | Kumar et al. |
| 2016/0038246 A1 | 2/2016 | Wang et al. |
| 2017/0007403 A1* | 1/2017 | Wildhirt ................ A61F 2/2481 |
| 2018/0001008 A1 | 1/2018 | Roehn et al. |
| 2019/0343589 A1 | 11/2019 | Kim et al. |

FOREIGN PATENT DOCUMENTS

| | | |
|---|---|---|
| SU | 921570 | 4/1982 |
| WO | 2009/088916 A1 | 7/2009 |

\* cited by examiner

EXOSKELETON FOR ASSISTING SURGICAL POSITIONING, METHOD FOR PRODUCING THE EXOSKELETON

This is the national stage of International Application PCT/HU2019/050049, filed Nov. 8, 2019.

The present invention relates to an exoskeleton for assisting surgical positioning, a method for producing the exoskeleton and a surgical method applying such an exoskeleton.

In surgical procedures, perfect positioning of surgical tools and the implantable devices on the anatomical surface of the organs or in the organs is an important issue. In particular, the appropriate surgical positioning has great importance at cardiac operations where a ventricular assist device is implanted into the heart of the patient.

Today the only definitive therapy for end-stage heart failure is heart transplantation (HTX). Heart transplantation has many drawbacks, such as, not all patients with end-stage heart failure are eligible for it, the lack of donors, risk of infection and tumor associated with immune suppression, The success of heart transplantation is strongly influenced by the patient's condition at the time of the operation. Mechanical circulatory support has a great role in stabilizing the patient's condition till the HTX, or treat conditions that could be relative contraindications to HTX for example poor renal or liver function, or pulmonary hypertension. Devices for mechanical circulatory support have been used for more than 40 years.

Nowadays the ventricular assist devices (VAD) are widely used to support either the left (left ventricular assist device-LVAD) or the right (right ventricular assist device-RVAD) or both ventricles (biventricular assist device-BiVAD) of the heart. There are devices available for short-mid term support (weeks to months), and long term support (years). In the short-mid term support group, the devices are not implantable, and the pumps are outside the body, whereas in the long term group, the devices are fully implantable, and connected to an energy source outside the body by a drive line.

In general the VADs actively drain the blood from a heart chamber, and pump the blood to a great vessel by a pump. This special pump is able to generate a flow up to 10 liters per minute, which is adequate to fulfill any patient need. The long-term LVAD is capable to support a patient for years, giving the patient a much better quality of life at home than any optimal medical therapy in end-stage heart failure.

It is known that the perfect positioning of the long-term LVAD inside the heart has a huge impact on the long-term outcome of this treatment. On the other hand, surgical positioning of these devices are only based on the surgeon's decision making, which is not reproducible, and not quantifiable. Any misplacement or wrong orientation of the LVAD device can cause hemodinamical instability, flow disturbances in the device or in the heart chamber, which will affect the patient clinical outcome.

Currently, the long-term LVAD implantation technique is based on the surgeon's decision making using intraoperative transesophageal echo scan to find the proper position for the long-term LVAD device implantation in the left ventricle. Several cases were reported in the scientific literature, where even with the intraoperative echocardiographic guidance, the implanted LVAD device twisted during the immediate postoperative period, or it was positioned improperly to such an extent that caused malfunction of the device.

There is a need to reduce the risk of LVAD misplacement. Therefore a tool to assist positioning the LVAD device to be implanted is required for practising and performing surgical procedures, thus decreasing the intraoperative and postoperative risks and improving clinical outcome.

The currently wide-spread 3D medical imaging (e.g. CT, MRI) and the quickly developing 3D printing technologies allow realistic spatial modeling of human or animal organs. Utilizing a model produced by 3D printing, the exact location and process can be determined before the surgery. Based on the 3D image and the 3D physical model, a positioning assistance device can be produced that accurately fits on the real organ.

The document US 2014/073907 discloses a system that summarizes, synergizes information obtained from several imaging models (PET, CT, MRI, MRSI, sonography, echocardiography, photoacoustic imaging and elastography). For image-guided surgical procedures the previously acquired images are combined with images obtained during the procedure, and changes during the intervention are modelled automatically, and thus, made into an image series which continuously follows it. These images will thereby form a real-time image series.

The document U.S. Pat. No. 8,303,505 relates to methods and devices used for image documentation and documentation of medical procedures. One of the solutions includes merging small field-of-view images with a large field-of-view image recorded, and real-time image of the small field-of-view with the recorded image with correlation of imaging data. To follow the imaging system a locating and orienting system may be used. The recorded image may be selected during the image parameter process based on real-time assessment of the heart parameter. Image manipulations planned on the base of recorded images may be stored and used for real-time informations also. The position of the medical device can be determined and fixed by visualizing the cursor on a three-dimensional image are in two non-parallel views.

The document US 2002/168618 relates to a system and a method for computer-simulation of image-guided diagnostic and therapeutic procedures. Simulation procedures mainly refer to the simulation of the following procedures: vascular catheterization, angioplasty, stent implantation, coil and graft implantation, embolotherapy and drug-infusion therapy. From one advantageous point of view, the system and the procedure were designed to look similar to a cardiovascular catheter laboratory where interventional radiological procedures were performed. One option is that the user applies therapeutic catheters, guide wires and other medical tools real-time in a way that the patient could be treated similarly by comparing patient-specific medical image data with the clinical procedure.

The document CN 106361429 relates to a method performing a simulated heart surgery. In this method, a real model of a patient's heart is produced by 3D imaging and 3D printing before surgery, and then by placing the model into a real surgical environment, a simulated surgery is carried out with the model. Congenital heart disorder operational plan preoperative 3D printing help performed evaluation support tool and method. After processing and assessing the data resulted from the simulation, the real surgery is carried out with the patient. This document also refers to congenital heart disorder operational plan preoperative 3D printing help performed evaluation support tool and method. The procedure includes steps used for acquiring thorax CT information of a normal person, a stereo structural model containing the heart and blood vessels with side branches of a normal person.

None of the above mentioned documents solve the problem of how to most accurately place a medical device onto an organ or into an organ to be operated at a surgery in a priorly planned position with the desired orientation.

It is an object of the present invention to provide a surgical positioning assistance device that precisely fits to an organ of a patient or a part of the organ and allows high-precision spatial positioning and orientation of a surgical tool to the organ during the surgical procedures.

It is a further object of the present invention to provide a method for producing such a surgical positioning assistance device easily and in a cost-effective way.

A further object of the invention is to provide a surgical method for precisely positioning and orienting a medical device or a surgical tool in an organ of a patient.

Due to the device and the methods of the present invention, more precise planning and operative execution are possible than before, thus minimizing the risks of the surgical procedures or the implantations.

The above object are achieved by providing an exoskeleton for assisting surgical positioning is made of biocompatible material and formed to be substantially form-preserving. The exoskeleton comprises a shell having a coupling surface fitting to at least a part of a surface of an organ to be operated, and a guiding channel is formed in the shell at a predetermined position, said guiding channel having a predetermined orientation with respect to said shell and a predetermined cross-sectional area for directing a surgical tool to the organ to be operated.

The above objects are further achieved by providing a method of producing an exoskeleton for assisting surgical positioning, the method comprising:
  recording images of an organ to be operated using a medical imaging apparatus;
  generating a 3D virtual model of the organ to be operated using a computer;
  determining a point or a surface area of the organ to be operated, to which a surgical tool is to be directed;
  generating a 3D virtual model of the exoskeleton using the computer, said model fitting to a surface of the 3D virtual model of the organ to be operated within the region of said determined point or surface area of the organ;
  identifying, using the computer, a position of the 3D virtual model of the exoskeleton, through which the surgical tool is to be directed to the organ to be operated;
  determining the orientation of insertion of the surgical tool with respect to the 3D virtual model of the exoskeleton;
  forming a guiding channel in the 3D virtual model 24 of the exoskeleton with a cross-sectional area suitable for guiding said surgical tool;
  based on the 3D virtual model of the exoskeleton, producing a real instance of the exoskeleton.

Finally, the above objects are achieved by providing a method for performing a surgery action on a patient, the method comprising:
  providing an exoskeleton according to the invention for an organ of the patient to be operated,
  attaching the exoskeleton to the organ by fitting anatomically identical points of the exoskeleton to the corresponding points of the outer surface of the organ,
  performing a surgical action on the organ at a predetermined position, using a surgical tool, wherein the surgical tool is advanced towards the organ with a predetermined orientation with respect to the organ by guiding surgical tool by means of said exoskeleton.

Preferred embodiments of the exoskeleton and the methods according to the invention are defined by the dependent claims.

The invention will now be described with reference to the accompanying drawings, in which.

Figure 1:
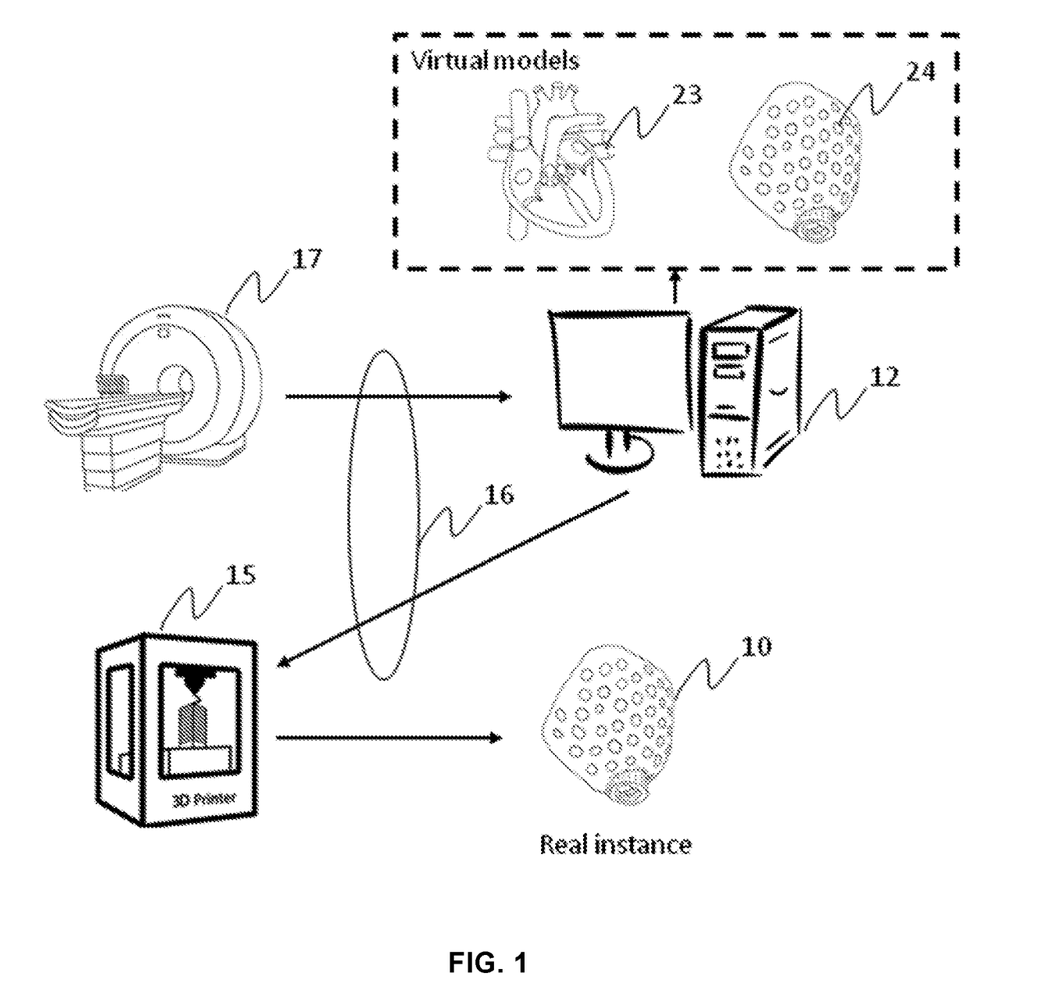
FIG. 1 is a schematic block diagram illustrative of the main components of a system for producing a surgical positioning assistance exoskeleton according to the present invention in an exemplary production of an exoskeleton used for a ventricular assist device.
Figure 2:
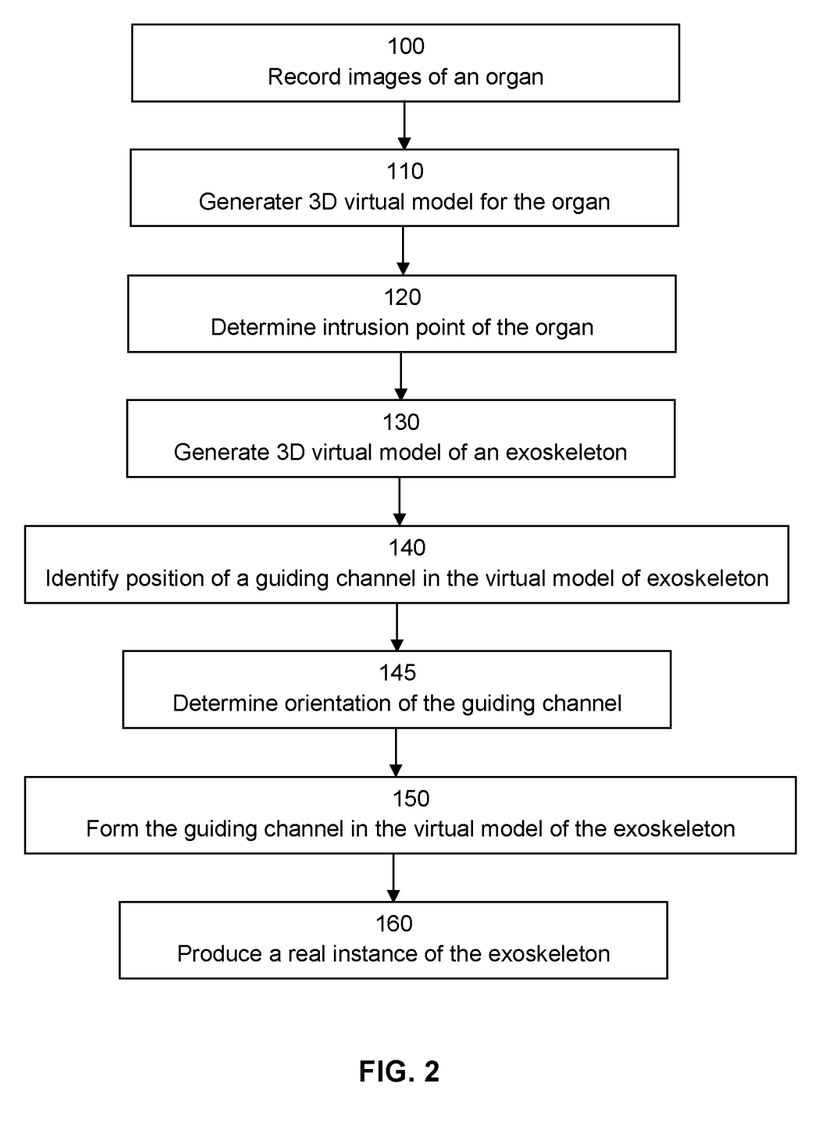
FIG. 2 is a flow diagram illustrative of the main steps of the production of a surgical positioning assistance exoskeleton according to the present invention.

The production process of a surgical positioning assistance exoskeleton, according to the present invention, is described below regarding FIGS. 1 and 2. FIG. 1 illustrates the main components of a system for producing a surgical positioning assistance exoskeleton according to the present invention in case of the production of an exoskeleton used for positioning a ventricular assist device. FIG. 2 is a flow diagram illustrative of the main steps of the production of an exoskeleton according to the present invention.

In the first step 100 of the production method, a plurality of images are recorded of the organ to be operated, for example, the heart of a patient, using a medical imaging apparatus 17, like CT, MRI or other apparatus. The raw images of the organ are forwarded in a standard image format, such as DICOM, to a computer 12 that, in step 110, based on the raw images of the organ, generates a 3D virtual model 23 of the organ using a specific computer program. It is preferred that in addition to the determination of the spatial shape of the organ in the modeling step, the computer 12 also creates a model for the internal structure and anatomy as well as fluid dynamics of the organ based on the raw images. Such 3D modeling computer softwares are well known in the art, and includes, among others, the Matlab (R2018b, The MathWorks, Inc., Natick, Massachusetts, US) and COMSOL Multiphysics (v. 5.4, COMSOL AB, Stockholm, Sweden), but depending on the particular field of application, any specific computer program may be developed for this purpose.

For modeling the outer shape, the inner structure and the blood flow or any other fluid flow of an organ, the computer 12 may preferably process pre-stored parameters, such as wall shear stress, wall tension, stasis, turbulence, thrombogenicity index, etc.

The parameters may be input by one or more professionals participating in the image and/or data or information processing. These data obtained from databases containing information relating to surgery, anatomy, fluid dynamics, modeling, etc. that may be used for 3D modeling.

In the next step 120, the computer 12 identifies a point or a surface area of the organ to be operated, to which the surgical assisting tool is to be fitted, and the computer 12 further determines the desired orientation of the surgical assisting tool with respect to the organ to be operated. For example, if a ventricular assist device has to be connected to the left ventricle of the heart, the computer 12 determines the epicardial and endocardial surfaces of the heart of the patient, with special regard to the detailed inner and outer surfaces of the left ventricle, as well as the wall thickness thereof. During the 3D modeling step, numerous structural and anatomical features of the organ to be operated may be determined so that the surgical assisting tool can be attached to the organ at an optimal position in the possibly most accurate manner.

Next, in step 130, a 3D virtual model 24 of an exoskeleton for the environment of the attachment point of the surgical assisting tool is generated by means of the computer 12, said the virtual model of the exoskeleton precisely fitting to the 3D virtual model 23 of the organ to be operated. The spatial extension and the thickness of the exoskeleton is determined on the basis of, among others, the physical properties of the organ to be operated, and other conditions to be respected to during the surgery (e.g., accessibility, sensibility, dangerous consequences of causing injury at specific points of the organ, etc.) For example, when a HeartMate 3™ ventricular assist device is to be implanted in the left ventricle of the heart, the 3D virtual model 24 of the exoskeleton is aligned to a segment having a diameter of ca. 4 cm at the apical region of the free wall of the left ventricle, and a suitable channel for the inflow cannula of the HeartMate 3™ ventricular assist device is created within this segment.

In the next step 140, based on the 3D virtual model 23 of the organ, the point of the 3D virtual model 24 of the positioning assistance exoskeleton, through which the surgical tool has to be attached to the organ to be operated, is identified, preferably partly or entirely by means of the computer 12. In step 145, the desired spatial orientation of the surgical tool relative to the organ to operated is determined, preferably partly or entirely by means of the computer 12, for the point of attachment. Based on these pieces of information, a guiding channel 22 is formed in the 3D virtual model 24 of the exoskeleton at the corresponding position, in step 150, using the computer 12. The guiding channel is formed to have the previously determined spatial orientation. As a result, the surgical tool can be attached to the organ optimally through the guiding channel of the guiding part. For example, when a ventricular assist device (e.g. HeartMate 3™ device) is to be implanted (e.g., to the left ventricle), the following geometric features of the patient's heart are preferably taken into account at forming the guiding part 22 of the positioning exoskeleton when generating the 3D virtual model 24 of the exoskeleton:

distance between the inflow cannula of the ventricular assist device and the interventricular septum;
inflow cannula axis keeping to the geometric mean of the plane of the mitral valve;
location of papillary muscles and left ventricular trabeculae related to the planned position of the inflow cannula.

It is particularly preferred that at least one of the following fluid dynamic characteristics of the patient's heart is also considered when generating the 3D virtual model of the exoskeleton:

turbulent flow;
shear stress in the region of the mitral annulus;
Wall tension;
Turbulence;
Stasis;
Thrombogenicity index;
Detection of retrograde flow and its potential effect on the formation of left ventricular thrombus.

After the 3D modeling step the exoskeleton 10, the model description data are forwarded to a manufacturing apparatus, for example in an ASCII or binary STL file format, Then in step 160, a real instance of the exoskeleton 10 is produced using the model description data. When the exoskeleton 10 is to be produced via 3D printing, the model description data are forwarded to a 3D printer 15 shown FIG. 2 and the exoskeleton 10 is produced by means of the 3D printer 15 using appropriate printing materials. It is also conceivable that the model description data are forwarded to a mould-forming apparatus, which is used to cast-mould or a press-mould, followed by producing the exoskeleton 10 using the mould, e.g., through injection moulding or pressing, etc.

The exoskeleton 10 is preferably made of a biocompatible, medical grade plastic material, in particular a polymeric material. For medical use, it is particularly preferred to use polylactic acid (PLA). PLA-based 3D printing can be performed, for example, by means of desktop 3D printers of the type Fused Deposition Modeling (FDM), such as the i3 MK3™ printer of Prusa Research.

The material of the exoskeleton 10 may also be any other biocompatible medical grade polymeric material, like nylon, silicone and polyetheretherketone (PEEK), as well as non-polymeric materials, in particular fabric made of absorbable material, bio-fabric; and metal, in particular titan, platinum or the alloys thereof.

Figure 3:
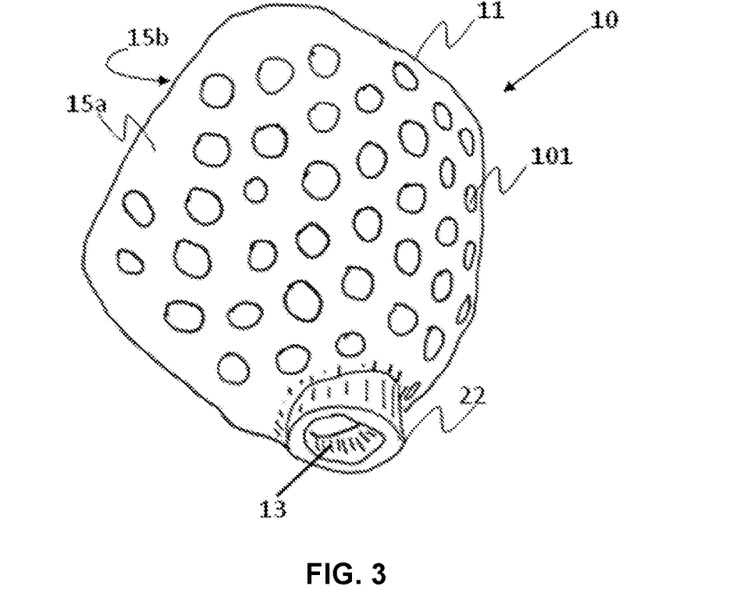
FIG. 3 is a schematic front view of an exemplary embodiment of the surgical positioning assistance exoskeleton used for a long-term ventricular assist device, according to the present invention.
Figure 4:
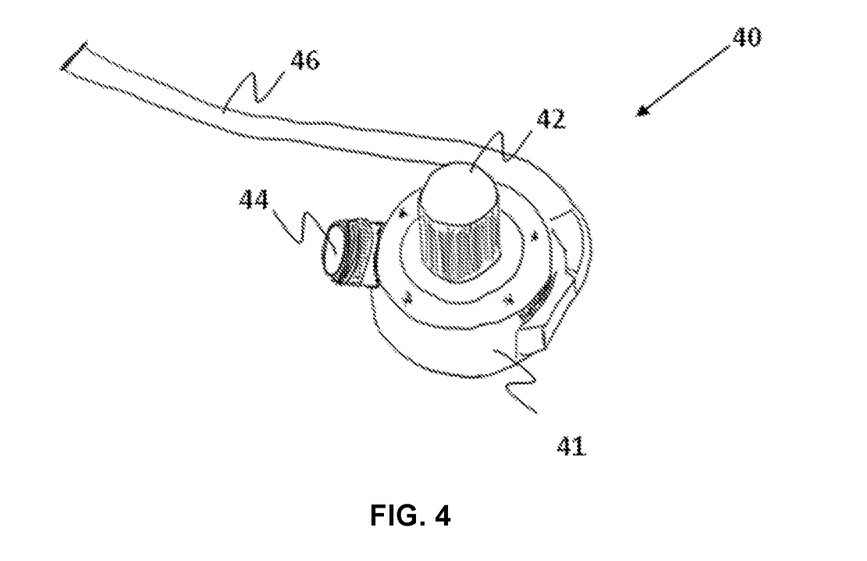
FIG. 4 schematically illustrates a long-term ventricular assist device for use with the exoskeleton shown in FIG. 3.

In FIG. 3, an exemplary embodiment of the surgical guiding exoskeleton according to the present invention is shown, which can be used to position a 20 a long-term LVAD as schematically shown in FIG. 4. The exoskeleton 10 has a comparatively thin, flexible, but form-preserving shell 11, with a thickness of 3-5 mm. Due to the 3D modelling, the exoskeleton 10 precisely fits to a corresponding outer surface region of the heart of the patient. At the position where the inflow cannula of the long-term LVAD is to be inserted into the left ventricle, the exoskeleton 10 contains a guiding part 22. This guiding part 22 comprises a guiding channel 13 for the apical coring knife which is inserted during the surgery for cutting the wall of the heart. The guiding channel 13 extends through the shell 11 of the exoskeleton 10. One end of the guiding channel 13 resides on the outer surface 15a of the shell 11, and its other end resides on the inner surface 15b of the shell 11. As this inner surface 15b will be fitted to the organ, this surface is also referred to as "coupling surface". The inner end of the guiding channel 13 is positioned so that after appropriately attaching the exoskeleton 10 to the organ, the inner end will match intrusion point of the organ, i.e. the surface point of the organ where the surgical tool is to be inserted into the organ.

Furthermore, the guiding channel 13 has a predetermined cross-sectional area that corresponds to the cross-sectional area of the surgical tool to be used. The cross-sectional area of the guiding channel 13 is formed and dimensioned so that the surgical tool can be guided therethrough with a minimal play.

The angle defined by the axis of the guiding channel 13 and the surface of the exoskeleton 10 determines the exact and preoperatively calculated position of the inflow cannula 24 of the long-term LVAD, so the LVAD can then be implanted into the patient's heart exactly at the desired position and with the desired orientation. The wall of the heart can be cut using a suitable apical coring knife guided through the guiding channel 13 of the exoskeleton 10. This kind of high-precision and well-planned surgical operation could significantly increase the intraoperative and postoperative patient safety, thus improving the clinical outcome.

In the above example, shown in FIG. 3, flexibility of the exoskeleton is limited to an extent that the exoskeleton is still capable of securely guiding the surgical tool in the intended direction.

In other applications of the exoskeleton according to the present invention, the exoskeleton may be produced as a substantially or entirely rigid piece.

As shown in FIG. 3, it is preferred that instead of a solid surface, the exoskeleton 10 may have a surface that comprises a plurality of apertures 101 in order to reduce its weight, so the exoskeleton 10 preferably has a net-like structure. The overall area of the apertures 101 and the arrangement thereof are such that the exoskeleton 10 can still preserve its shape to substantial extent, thus allowing accurate fitting to the organ to be operated during a surgery.

Due to the 3D imaging and the 3D printing, the exoskeleton according to the invention is produced uniquely for each patient with taking the needs and the limitations of the surgery into account, offering a personalised solution to each patient. The 3D imaging, the computer-aided image processing and model generation, as well as the 3D printing and the surgery itself may be carried out at different locations. In one embodiment of the production method, the raw image data are forwarded from the medical imaging apparatus 17 to a central computer 12 through wired and/or wireless communication system 16 (e.g. LAN, WLAN, internet, mobile communication system, etc.), said computer 12 carrying out the 3D imaging and 3D model generation. The professionals may influence the processes of the central computer 12 either locally or remotely, via a terminal device. The model description data of the 3D virtual model of the exoskeleton may also be forwarded from the computer 12 to the 3D printer 15 through wired and/or wireless communication system(s) 16. It is particularly preferred that the step of 3D printing is carried out in a sterile room, where the printed instance of the exoskeleton is immediately packaged for transportation to the sterilization unit.

Figure 5:
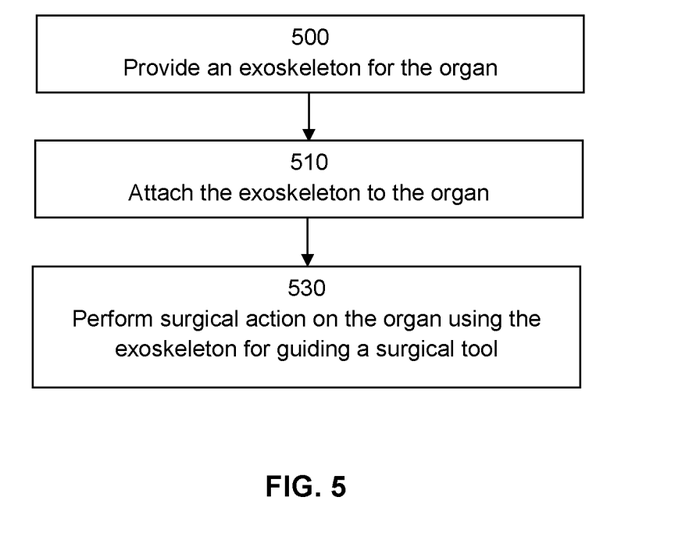
FIG. 5 is a flow diagram illustrative of the main steps of the surgical application of the surgical positioning assistance exoskeleton according to the present invention.

The main steps of the surgical application of the exoskeleton according to the invention is described below with reference to the flow diagram shown in FIG. 5.

In the first step 500 of the surgical method, an exoskeleton that has been previously produced for the particular organ of the patient by the above mentioned production method, preferably by 3D printing.

In the next step 510, the exoskeleton 10 is attached to the organ by fitting the anatomically corresponding points of the exoskeleton 10 to the outer surface of the organ, e.g. the heart. Due to its form-preserving configuration, the exoskeleton 10 exactly fits to the outer surface of the given organ.

To implant a long-term LVAD (e.g. HeartMate 3™) into the left ventricle an orifice is to be formed on the left ventricle, perfectly sized to the inflow cannula of the long-term LVAD.

This orifice is made by a coring knife to achieve the best result at the pre-planned position with the pre-planned orientation. Such a long-term LVAD device is schematically illustrated in FIG. 4. The LVAD device 40 comprises a blood pump 41, an inflow cannula 42, an outflow cannula 44 and a drive line 46.

In the next step 520 of the method, the exoskeleton 10 is placed on the organ to be operated. The fixation can be carried out manually. It is important that during the positioning or at removal of the exoskeleton 10, it should not cause injury to the organ to be operated and/or other organs of the patient.

After the exoskeleton 10 is fixed on the surface of the organ (e.g. heart), the surgical tool (e.g. coring knife) is guided through the exoskeleton's guiding channel in step 530, and the orientation of the surgical tool is directed by the 3D orientation of the exoskeleton 10.

During the cardiac surgical implantation of a long-term LVAD the coring knife is inserted first into the guiding channel of the guiding part of the exoskeleton 10. Secondly it is advanced and rotated towards the wall of the heart (e.g. the left ventricle), creating a hole in the wall. Through this hole the inflow cannula 42 of the long-term LVAD 40 shown in FIG. 4 (e.g. HeartMate 3™) can be implanted.

With the exoskeleton 10 the position and the orientation of insertion of the surgical tool (e.g. a coring knife) is identical to the pre-planned insertion position and orientation of the organ to be operated, so the subsequent steps of the surgery (e.g. implantation of the ventricular assist device) can be carried out in the optimal way.

In a further optional step of the surgical method, when the exoskeleton 10 is made of a polymer or other non-absorbable material, the exoskeleton 10 is removed from the surface of the organ. When the aim of the surgical method is to prepare for the implantation of a medical device, for example formation of a hole in the wall of the heart for receiving the inflow cannula 42 of a long-term LVAD 40 shown in FIG. 4, after removal of the exoskeleton 10, the surgical implantation can be completed.

The foregoing description of disclosed embodiments provides illustration and description only, but is not intended to be exhaustive or to limit the invention to the precise form disclosed. Modifications and variations are possible in light of the above teachings or may be acquired from practice of the disclosure.

The invention claimed is:

1. An exoskeleton (10) and an associated apical coring knife, the exoskeleton (10) for assisting surgical positioning of the apical coring knife, wherein the overall exoskeleton (10) is formed as a single part, made of biocompatible material and formed to be substantially form-preserving, the exoskeleton (10) comprises a shell (11) having a unique patient-specific surface (15b) configured to fit to and to directly contact with at least a part of a surface of a patient's heart to be operated, the exoskeleton comprises a cylindrical guiding channel (13) extending through the shell (11) and located at a specific position of the shell, and said guiding channel (13) has a specific longitudinal direction with respect to said shell (11) and a specific cross-section identical to a cross-section of the apical coring knife associated with the exoskeleton, wherein the guide channel (13) has a substantial length and the guiding channel (13) is configured to guide said associated apical coring knife directly along said specific longitudinal direction in said guiding channel (13).

2. The exoskeleton (10) and associated apical coring knife according to claim 1, wherein the shell is provided with a plurality of apertures (101).

3. The exoskeleton (10) and associated apical coring knife according to claim 1, wherein the material of the exoskeleton (10) is selected from the group consisting of the following biocompatible materials: polymeric material, absorbable fabric, bio-fabric, and metal.

4. A method of producing the exoskeleton (10) and associated apical coring knife according to claim 1, characterized in that the method comprises recording (100) images of a heart to be operated on;
generating (110) a 3D virtual model of the heart to be operated on using a computer;

determining (120) a point or a surface area of the heart to be operated on, to which the apical coring knife is to be directed;

generating (130) a 3D virtual model of the exoskeleton (10) using the computer, said 3D virtual model of the exoskeleton fitting to a surface of the 3D virtual model of the heart to be operated on within a region of said determined point or surface area of the heart to be operated on;

identifying (140), using the computer, a position of the 3D virtual model of the exoskeleton (10), through which the apical coring knife is to be directed to the heart to be operated on;

obtaining anatomic features and flow dynamics features of the heart to be operated on from the recorded images of the heart; and determining (145) the orientation of insertion of the apical coring knife with respect to the 3D virtual model of the exoskeleton (10) based on said anatomic features and said flow dynamics features;

forming (150) a guiding channel in the 3D virtual model of the exoskeleton (10) with said determined position and orientation and with a cross-sectional area suitable for guiding said apical coring knife;

based on the 3D virtual model of the exoskeleton (10), producing (160) a substantially form-preserving real instance of the exoskeleton (10).

5. The method according to claim 4, wherein said real instance of the exoskeleton (10) is produced from biocompatible polymeric material through 3D printing.

6. The method according to claim 4, wherein said real instance of the exoskeleton (10) is produced from biocompatible polymeric material through injection moulding or pressing.

7. A method for performing apical coring on a patient's heart using an apical coring knife characterized in that the method comprises:

providing (500) the exoskeleton (10) according to claim 1 for the heart of the patient to be operated on, attaching (510) the exoskeleton (10) to the heart by fitting anatomically identical points of the exoskeleton (10) to corresponding points of an outer surface of the heart, performing (530) apical coring on the heart at a specific position, using the apical coring knife, wherein the coring knife is advanced towards the heart along a specific direction with respect to the heart through the cylindrical guiding channel of said exoskeleton (10).

8. The method of claim 7, wherein the step of attaching the exoskeleton (10) to the heart comprises manually fixing the exoskeleton (10) to the heart.

9. The exoskeleton (10) and associated apical coring knife according to claim 3, wherein the polymeric material is polylactic acid (PLA), polyetheretherketone (PEEK), nylon, or silicone; and the metal is titanium, platinum, or alloys thereof.

10. The exoskeleton (10) and associated apical coring knife according to claim 1 wherein the exoskeleton (10) is made by a method comprising recording (100) medical images of the heart to be operated on;

generating (110) a 3D virtual model of the heart to be operated on using a computer;

determining (120) a point or a surface area of the heart to be operated on, to which the apical coring knife is to be directed;

generating (130) a 3D virtual model of the exoskeleton (10) using the computer, said 3D virtual model of the exoskeleton (10) fitting to a surface of the 3D virtual model of the heart to be operated on within a region of said determined point or surface area of the heart;

identifying (140), using the computer, a position of the 3D virtual model of the exoskeleton, through which the apical coring knife is to be directed to the heart to be operated on;

obtaining anatomic features and flow dynamics features of the heart to be operated on from the recorded images of the heart; and determining (145) an orientation of insertion of the apical coring knife with respect to the 3D virtual model of the exoskeleton (10) based on said anatomic features and said flow dynamics features;

forming (150) a guiding channel in the 3D virtual model of the exoskeleton (10) with said determined position and orientation and with a cross-sectional area suitable for guiding said apical coring knife; and based on the 3D virtual model of the exoskeleton (10), producing (160) a substantially form-preserving real instance of the exoskeleton (10).

\* \* \* \* \*